United States Patent [19]

Rao

[11] Patent Number: 5,447,896
[45] Date of Patent: Sep. 5, 1995

[54] HYDRODEHALOGENATION CATALYSTS AND THEIR PREPARATION AND USE

[75] Inventor: V. N. Mallikarjuna Rao, Wilmington, Del.

[73] Assignee: E. I. du Pont de Nemours and Company, Wilmington, Del.

[21] Appl. No.: 152,937

[22] Filed: Nov. 15, 1993

Related U.S. Application Data

[63] Continuation of Ser. No. 903,030, Jun. 23, 1992, abandoned.

[51] Int. Cl.⁶ .................. B01J 21/18; B01J 23/40; B01J 23/52
[52] U.S. Cl. .................. 502/184; 502/185; 502/330; 570/176
[58] Field of Search .............. 502/180, 184, 185, 330

[56] References Cited

U.S. PATENT DOCUMENTS

| | | | |
|---|---|---|---|
| 4,097,368 | 6/1978 | Hayes | 585/752 |
| 5,053,377 | 10/1991 | Lerot et al. | 502/184 |
| 5,094,988 | 3/1992 | Kellner et al. | |
| 5,136,113 | 8/1992 | Rao | |
| 5,149,680 | 9/1992 | Kitson et al. | 502/184 |

FOREIGN PATENT DOCUMENTS

| | | |
|---|---|---|
| 0347830 | 6/1989 | European Pat. Off. |
| 1-128942 | 11/1987 | Japan |
| 2-218626 | 2/1989 | Japan |
| 1578933 | 5/1977 | United Kingdom |

*Primary Examiner*—Anthony McFarlane

[57] ABSTRACT

A carbon-supported metal hydrodehalogenation catalyst is disclosed which is prepared by impregnating a carbon support having an ash content of less than about 0.2% by weight (based on the weight of said support) with a combination of metals consisting essentially of from 5 to 95 parts by weight gold and from 95 to 5 parts by weight total ruthenium, rhodium, palladium, osmium, iridium, and/or platinum; and treating said impregnated carbon composition to dry the composition and to provide metal of said combination in a reduced state, the impregnation of treatment being accomplished at a temperature of about 350° C. or less. The advantageous use of the catalyst for the catalytic hydrogenolysis of fluorohalocarbons and fluorohalohydrocarbons is also disclosed.

9 Claims, No Drawings

HYDRODEHALOGENATION CATALYSTS AND THEIR PREPARATION AND USE

This is a continuation of application Ser. No. 07/903,030, filed Jun. 23, 1992, now abandoned.

BACKGROUND OF THE INVENTION

1. Field of the Invention

This invention relates to hydrodehalogenation catalysts and their use for the catalytic hydrogenolysis of fluorohalocarbons or fluorohalohydrocarbons and more particularly to carbon supported metal catalysts containing gold and their use in the hydrogenolysis of fluorohalocarbons or fluorohalohydrocarbons.

2. Background

A number of chlorinated fluorocarbons are considered to be detrimental toward the Earth's ozone layer. There is a world-wide effort to develop materials that can serve as effective replacements. For example, 1,1,1,2-tetrafluoroethane (HFC-134a), a hydrofluorocarbon containing no chlorine, is being considered as a replacement for dichlorodifluoromethane (CFC-12) in refrigeration systems because of its zero ozone depletion potential. There is thus a need for manufacturing processes that provide fluorocarbons that contain less chlorine.

One method of reducing the chlorine content of halogen substituted hydrocarbons containing chlorine as well as fluorine is reacting organic starting materials containing chlorine and fluorine with hydrogen at elevated temperature in the presence of a hydrogenation catalyst (e.g., supported Group VII or Group VIII metal catalysts). British Patent Specification 1,578,933 discloses, for example, that HFC-134a can be prepared by the hydrogenolysis of 2,2-dichloro-1,1,1,2-tetrafluoroethane (CFC-114a) or 1,1,1,2-tetrafluorochloroethane (HCFC-124) over palladium on carbon or palladium on alumina hydrogenation catalysts. There remains a continued interest in providing improved hydrogenolysis processes for the manufacture of HFC-134a as well as other fluorohydrocarbons and fluorohalohydrocarbons.

Techniques for enhancing the durability of Group VIII metal hydrogenolysis catalysts have been disclosed. The catalyst improvements described in Eur. Pat. Appln. 347,830 and Jap. Pat. Appln. 1-128,942 are achieved by the addition of other elements, such as Group IB (e.g., gold), lanthanum, lanthanide elements, and rhenium to the Group VIII metal catalysts. The additives are said to prevent sintering and also increase the durability and the mechanical strength of the catalysts. In general, the mixed metal catalysts are dried at 500° C. to 550° C. and are then reduced (e.g., with hydrogen).

SUMMARY OF THE INVENTION

This invention provides a highly active carbon-supported metal hydrodehalogenation catalyst, and a method for its preparation. The method for preparing the hydrodehalogenation catalyst of this invention comprises the steps of impregnating a carbon support having an ash content of less than about 0.2% by weight (based on the weight of said support) with a combination of metals consisting essentially of from 5 to 95 weight percent gold (based upon the weight of the metal combination) and from 95 to 5 weight percent total ruthenium, rhodium, palladium, osmium, iridium, and/or platinum at a temperature of about 350° C. or less; and treating said impregnated carbon composition at a temperature of about 350° C. or less to dry the composition and to provide metal of said combination in a reduced state. This invention provides a process for the catalytic hydrogenolysis of fluorohalocarbons and fluorohalohydrocarbons which is characterized by using said catalyst and operating at a temperature within the range of from about 125° C. to 350° C.

DETAILS OF THE INVENTION

This invention involves catalysts prepared by impregnating a carbon support having an ash content of less than about 0.2%, with a combination of metals including gold and another metal (e.g., palladium) and then treating the impregnated carbon to dry the composition and to provide metal of said combination in a reduced state. In accordance with this invention, both the impregnation and the subsequent treatment are conducted at a temperature of about 350° C. or less.

Suitable catalyst supports may be prepared by treating the carbon to be used as the catalyst support with acid. Typically the support is then washed with deionized water and dried; and the metal is then deposited thereon using deposit techniques well known in the art (e.g., using catalyst precursors such as gold chloride and palladium chloride). Typically the carbon is treated with an acid other than hydrofluoric acid which contains neither phosphorus nor sulfur such that after such treatment the carbon contains less than about 0.2% by weight ash. A second acid treatment using hydrofluoric acid may also be used. Preferably, the carbon is treated with two acids such that after such treatment the carbon contains less than about 0.1% by weight ash. Reference is made to U.S. Pat. No. 5,136,113 which is hereby incorporated herein in its entirety, for further discussion of advantageous use of carbon supported catalysts having a low ash content.

Preferably, after acid treatment and the subsequent deposit of the metal component, the catalyst also contains less than about 200 ppm phosphorus and less than about 200 ppm sulfur; more preferably less than 100 ppm phosphorus and less than 100 ppm sulfur; and most preferably less than 50 ppm phosphorus and less than 50 ppm sulfur. The preferred catalysts of this invention also contain less than about 100 ppm potassium. Washing the carbon with acid(s) that remove excess potassium as well as phosphorus and sulfur is thus particularly preferred. Most preferably the catalyst of this invention contain less than about 100 ppm sodium and/or less than about 100 ppm iron. Accordingly, washing with acid(s) that remove excess sodium and iron is especially preferred. Reference is made to U.S. patent application Ser. No. 07/633,922, now abandoned, which is hereby incorporated herein in its entirety, for further discussion of advantageous use of carbon supported catalysts having a low content of phosphorus, sulfur, potassium, sodium and/or iron. Commercially available carbons which may be treated with acids to provide suitable supports include those sold under the following trademarks: Darco ™, Nuchar ™, Columbia SBV ™, Columbia MBV ™, Columbia MBQ ™, Columbia JXC ™, Columbia CXC ™, Calgon PCB ™, and Barnaby Cheny NB ™. The carbon support can be in the form of powder, granules, or pellets, etc.

Examples of acids which may be used for acid washing during the catalyst preparation process include organic acids such as acetic acid and inorganic acids, e.g., HCl or HNO$_3$. Preferably hydrochloric acid or nitric acid is used. The acid treatment may be accomplished in several ways. A preferred embodiment is described below.

A carbon support is soaked overnight with gentle stirring in a 1 molar solution of the acid prepared in deionized water. The carbon support is then separated and washed at least 10 times with deionized water or until the pH of the washings is about 3. (Preferably, the carbon support is then soaked again with gentle stirring in a 1 molar solution of the acid prepared in deionized water for 12 to 24 hours.) The carbon support is then finally washed with deionized water until the washings are substantially free of the anion of the acid (e.g., Cl$^-$ or NO$_3^-$), when tested by standard procedures. The carbon support is then separated and dried at 120° C. The washed carbon is then, if desired, soaked in 1 molar HF prepared in deionized water for 48 hours at room temperature with occasional stirring (e.g., in a plastic beaker). The carbon support is separated and washed repeatedly with deionized water at 50° C. until the pH of the washings is greater than 4. The carbon support is then dried at 150° C. for 60 hours in air followed by calcination at 300° C. for 3 hours in air prior to its use as a support.

The carbon support is impregnated with the combination of metals at a temperature of about 350° C. or less. Suitable metal combinations consist essentially of from 5 to 95 parts by weight gold and from 95 to 5 parts by weight total of ruthenium, rhodium, palladium, osmium, iridium, and platinum. Metal combinations consisting essentially of gold and palladium are preferred. The metal components are preferably mixed and impregnated on the low ash carbon support in a conventional manner using aqueous solutions of metal salts. Typically this includes contacting the carbon with the aqueous salt solution(s), draining excess solution from the carbon, and washing with deionized water to remove excess anions. In order to concentrate the metal content of the outer carbon surface, the carbon may be impregnated with pure water prior to contact with the aqueous solution(s) of metal salts.

In accordance with the catalyst preparation of this invention the impregnated carbon is treated at a temperature of about 350° C. or less to dry the composition and to provide metal in a reduced state. This may be accomplished by first drying the impregnated carbon in air, typically at about 130°–150° C., and then heating the dried composition in a reducing atmosphere (e.g., H$_2$) at a temperature within the range of about 150° C. to 350° C. Typically, the combination of metals will constitute between about 0.1 to 10 percent by weight of the catalyst. Preferably, the combination of metals will constitute about 1% by weight although it is believed that higher amounts may be desirable in some embodiments.

Without limiting the invention to a particular theory of operation, it is believed that impregnation and treatment at 350° C. or less produces a carbon-supported alloy catalyst with advantageous alloy dispersion. An alloy consisting essentially of from about 50 to 70 weight percent gold and from 50 to 30 weight percent palladium is especially preferred.

The fluorohalocarbons and/or fluorohalohydrocarbons used in the hydrogenolysis reactions of this invention are preferably those wherein halo is chloro or bromo. Included are fluorohalocarbons consisting of carbon, fluorine and at least one of chlorine and bromine; and fluorohalohydrocarbons, consisting of carbon, fluorine, hydrogen, and at least one of chlorine and bromine. Hydrogenolysis of chlorofluorocarbons (i.e., CFCs) and hydrochlorofluorocarbons, (i.e., HCFCs) is thus provided by this invention. Suitable fluorohalocarbons and fluorhalohydrocarbons may contain 1 to 6 carbon atoms, and include the cyclic as well as acyclic compounds represented by the empirical formula $C_nH_mF_pX_q$, wherein each X is independently selected from Cl and Br, and is preferably Cl, and wherein n is an integer from 1 to 6, m is an integer from 0 to 12, p is an integer from 1 to 13, and q is an integer from 1 to 13, provided that m+p+q equals 2n+2 when the compound is saturated and acyclic, equals 2n when the compound is saturated and cyclic or is olefinic and acyclic, and equals 2n−2 when the compound is olefinic and cyclic. The hydrogenolysis process produces predominantly saturated products.

Preferred applications include hydrogenolysis of compounds containing 1 to 3 carbon atoms. Examples of acyclic compounds which undergo hydrogenolysis include 1,1,1,2-tetrachloro-2,2-difluoroethane (CFC-112a), which may be hydrogenolyzed to 1,1-difluoroethane (HFC-152a); 1-chloro-1,1-difluoroethane (HCFC-142b) which may be hydrogenolyzed to 1,1-difluoroethane (HFC-152a); 1,1,2-trichloro-1,2,2-trifluoroethane (CFC-113) which may be hydrogenolyzed to 1,1-dichloro-1,2,2-trifluoroethane (HCFC-123a); 1,1,1-trichloro-2,2,2-trifluoroethane (CFC-113a) which may be hydrogenolyzed to 2,2,-dichloro-1,1,1,-trifluoroethane (HCFC-123); 1,2-dichloro-1,1,2,2-tetrafluoroethane (CFC-114) which may be hydrogenolyzed to 1-chloro-1,1,2,2-tetrafluoroethane (HCFC-124a) and 1,1,2,2, -tetrafluoroethane (HFC-134); 2,2-dichloro-1,1,1,2-tetrafluoroethane (CFC-114a), which may be hydrogenolyzed to 2-chloro-1,1,1,2-tetrafluoroethane (HCFC-124) and 1,1,1,2-tetrafluoroethane (HFC-134a); HCFC-124 itself which may be hydrogenolyzed to HFC-134a; and 2,2-dichloro-1,1,1,3,3,3-hexafluoropropane (CFC-216aa) which may be hydrogenolyzed to 1,1,1,3,3,3-hexafluoropropane (HFC-236fa) . Examples of cyclic compounds include 4,5-dichloro-1,1,2,2,3,3-hexafluorocyclopentane which may be hydrogenolyzed to 1,1,2,2,3,3-hexafluorocyclopentane.

In a preferred embodiment the fluorohalocarbons and/or fluorhalohydrocarbons are represented by the above empirical formula where n is 1 to 3, m is 0 to 6, p is 1 to 7, and q is 1 to 7.

In accordance with this invention the fluorohalocarbon(s) and/or fluorohalohydrocarbon(s) to be hydrogenolyzed are reacted with hydrogen at an elevated temperature in the presence of the low ash content carbon supported catalysts disclosed herein. Suitable temperatures are about 350° C. or less. Typically the reaction is carried out at a temperature which is at least about 125° C. Preferred temperatures depend to some extent upon the particular fluorohalocarbon(s) and/or fluorohalohydrocarbon(s) to be reacted.

A conventional amount of hydrogen is used. Generally, in order to provide substantial hydrogenolysis product yields, the amount of hydrogen used is at least about 0.5 moles per mole of fluorohalocarbon and/or fluorohalohydrocarbon used. To provide yields desired in many embodiments, at least stoichiometric amounts of hydrogen are used. Hydrogen in considerable excess of the stoichiometric amount (e.g., ten times the stoichiometric amount) may also be used.

The hydrogenolysis of fluorohalocarbons or fluorohydrohalocarbons can be performed in liquid-phase or vapor-phase using well-known chemical engineering practice, which includes continuous, semi-continuous or batch operations. The hydrogenolysis process is typically achieved at atmospheric or superatmospheric pressures.

In some embodiments, it is preferred to pretreat the catalyst prior to hydrogenolysis. For example, in the vapor-phase hydrogenolysis of CFC-114a to HFC-134a, it is preferred to pretreat the catalyst with CFC-114a prior to adding hydrogen (see e.g., U.S. Pat. No. 5,094,988).

Practice of the invention will become further apparent from the following non-limiting examples.

EXAMPLES

General Procedure for Product Analysis

The products leaving the reactor were analyzed on line using a gas chromatograph. The column had a 6.1 m×3.2 mm (20 ft.×⅛ in.) stainless steel tube containing Krytox ™ perfluorinated polyether on an inert support. Helium was used as the carrier gas. The product analyses are reported in area percent.

EXAMPLE 1

Au (60 wt. %)/Pd (40 wt. %) on Carbon Catalyst Preparation

A sample of HCl washed coconut-based carbon (50 g, 4.8 mm×2.4 mm (4×8 mesh)) having an ash content of about 0.15% (including about 12 ppm Fe, about 11 ppm Na, about 90 ppm K, and about 400 ppm Si) was soaked in deionized water to saturate the pores. It was then drained on a porous frit to remove excess water. To the drained carbon was added a solution containing 0.46 g $AuCl_3$, 0.33 g $PdCl_2$ and 2.0 mL conc. HCl in 250 mL deionized water. The mixture was gently stirred for about 5 minutes. It was then drained dry and divided into two parts.

A: One sample was dried in air at 150° C. for five hours followed by hydrogen reduction at 300° C. for five hours. X-ray analysis showed the presence of a gold/palladium alloy.

B: The other sample was dried in air at 150° C. for five hours followed by heating under a nitrogen stream at 550° C. for four hours. It was then reduced in a stream of hydrogen at 300° C. for five hours.

EXAMPLE 2

2,2-Dichloro-1,1,1,2-tetrafluoroethane Hydrogenolysis

A 1.3 cm×15.2 cm (0.5"×6") reactor contained in a fluidized sand bath was charged with 10 cc of the catalyst prepared according to 1A or 1B above. A flow of 10 cc/min CFC-114a and 20 cc/min hydrogen was passed through the reactor maintained at 150° C. The performance of the two catalysts prepared according to 1A or 1B after 16 hours from the initiation of the reaction is shown in Table 1.

TABLE 1

| Catalyst Prep. | % Conv. 114a[1] | % Selectivity to | | |
|---|---|---|---|---|
| | | 134a[2] | 124[3] | 143a[4] |
| 1A | 35.7 | 84.2 | 12.1 | 3.7 |

TABLE 1-continued

| Catalyst Prep. | % Conv. 114a[1] | % Selectivity to | | |
|---|---|---|---|---|
| | | 134a[2] | 124[3] | 143a[4] |
| 1B | 3.4 | 69.9 | 11.6 | 18.5 |

[1] 114a = $CF_3CFCl_2$
[2] 134a = $CF_3CH_2F$
[3] 124 = $CF_3CFHCl$
[4] 143a = $CF_3CH_3$

EXAMPLE 3

2-Chloro-1,1,1,2-tetrafluoroethane Hydrogenolysis

Example 1 was substantially repeated except that the feed to the reactor was 10 cc/min of HCFC-124 and 10 cc/min of hydrogen and the reactor temperature was 250° C. The performance of the two catalysts prepared according to 1A and 1B after 18 hours from the initiation of the reaction is summarized in Table 2.

TABLE 2

| Catalyst Prep. | % Conv. 124 | % Selectivity to | |
|---|---|---|---|
| | | 134a | 143a |
| 1A | 33.4 | 96.0 | 4.0 |
| 1B | 5.1 | 92.9 | 7.1 |

Comparison of the data in Tables 1 and 2 show that catalyst made by the process of 1B, where it was heated to 550° C. under a nitrogen stream, both conversion and selectivity are inferior when compared to the performance of catalyst made by the process of 1A where the catalyst was not subjected to a high temperature treatment under a nitrogen stream.

EXAMPLE 4

Au(10 wt. %)/Pd(90 wt. %) on Carbon Catalyst Preparation

A 100 g sample of 4.8 mm×2.4 mm (4×8 mesh) of the HCl washed coconut-based carbon used in Example 1 was soaked in 160 mL of deionized water at room temperature for about 60 hr. At the end of this period an additional 250 mL of deionized water was added. The mixture was gently stirred and a solution of 0.75 g $PdCl_2$, 0.077 g $AuCl_3$, 8.69 mL 1M HCl, and 250 mL deionized water was added over 15 min. It was allowed to stand for an additional 30 min. at room temperature and drained on a porous plate using aspirator vacuum.

A 92.8 g sample of the above wet carbon was washed six times with about 150 mL of deionized water for each washing. It was again drained on a porous plate using aspirator vacuum and subsequently dried in air at 150° C. for five hours to give 49.7 g of the dried material. This dried material was divided into four equal parts and additionally treated as shown below.

C: The first sample was reduced in a stream of hydrogen at 250° C. for four hours.

D: The second sample was heated in a stream of nitrogen at 500° C. for four hours. It was then cooled to 250° C. and reduced in a stream of hydrogen at this temperature for four hours.

E: The third sample was reduced in a stream of hydrogen at 275° C. for four hours.

F: The fourth sample was heated in a stream of nitrogen at 550° C. for four hours. It was then cooled to 275° C. and reduced in a stream of hydrogen for four hours.

EXAMPLE 5

2,2-Dichloro-1,1,1,2-tetrafluoroethane Hydrogenolysis

Example 2 was substantially repeated using 10 cc of catalyst prepared according to 4C or 4D. Results obtained after about 16 hours from the initiation of the reaction are shown in Table 3.

TABLE 3

| Catalyst | % Conv. | % Selectivity to | | |
|---|---|---|---|---|
| Prep. | 114a | 134a | 124 | 143a |
| 4C | 31.5 | 90.4 | 7.1 | 2.5 |
| 4D | 5.2 | 76.8 | 9.4 | 13.8 |

EXAMPLE 6

2-Chloro-1,1,1,2-tetrafluoroethane Hydrogenolysis

Example 3 was substantially repeated using 10 cc of catalyst prepared according to 4C or 4D. Results obtained after about 28 hours of operation are shown in Table 4.

TABLE 4

| Catalyst | % Conv. | % Selectivity to | |
|---|---|---|---|
| Prep. | 124 | 134a | 143a |
| 4C | 26.7 | 97.7 | 2.3 |
| 4D | 5.4 | 96.4 | 3.6 |

Comparison of the data in Tables 3 and 4 show that catalyst heated to a high temperature under nitrogen which was prepared according to 4D, is a much less active catalyst for the hydrogenolysis of CFC-114a. It is also less selective for the desired HFC-134a and HCFC-124. In addition, it is much less active active for the hydrogenolysis of HCFC-124 to HFC-134a.

EXAMPLE 7

2,2-Dichloro-1,1,1,2-tetrafluoroethane Hydrogenolysis

Example 2 was substantially repeated using 10 cc of catalyst prepared according to 4E or 4F. Results obtained after about 14 hours of operation are shown in Table 5.

TABLE 5

| Catalyst | % Conv. | % Selectivity to | | |
|---|---|---|---|---|
| Prep. | 114a | 134a | 124 | 143a |
| 4E | 31.2 | 90.1 | 7.4 | 2.5 |
| 4F | 4.9 | 75.5 | 10.4 | 14.1 |

Comparison of the data in Table 5 shows that the catalyst prepared according to 4F, which was heated to 550° C. is much less active for the conversion of CFC-114a and is also less selective for HFC-134a and HCFC-124.

Particular embodiments of the invention are included in the Examples. Other embodiments will become apparent to those skilled in the art from a consideration of the specification or practice of the invention. It is understood that modifications and variations may be practiced without departing from the spirit and scope of the novel concepts of this invention. It is further understood that the invention is not confined to the particular formulations and examples herein illustrated, but it embraces such modified forms thereof as come within the scope of the claims.

What is claimed is:

1. A method of preparing a hydrodehalogenation catalyst comprising the steps of:

impregnating a carbon support having an ash content of less than about 0.2% by weight, with a combination of metals consisting essentially of from 5 to 95 weight percent gold and from 95 to 5 weight percent total of at least one metal selected from the group consisting of ruthenium, rhodium, palladium, osmium, iridium, and platinum at a temperature of about 350° C. or less; and treating said impregnated carbon composition by drying in air at a temperature of about 130° to about 150° C. and then heating in a reducing atmosphere at a temperature of about 350° C. or less to provide metal of said combination in a reduced state.

2. A method of preparing a hydrodehalogenation catalyst comprising the steps of:

impregnating a carbon support having an ash content of less than about 0.2% by weight, with a combination of metals consisting essentially of from 5 to 95 weight percent gold and from 95 to 5 weight percent total of at least one metal selected from the group consisting of ruthenium, rhodium, palladium, osmium, iridium, and platinum; and treating said impregnated carbon composition to provide metal of said combination in a reduced state; said treatment including drying the impregnated carbon composition and heating the dried composition in a reducing atmosphere; and said impregnation and treatment being at a temperature of about 350° C. or less.

3. A carbon-supported metal hydrodehalogenation catalyst having a carbon support impregnated with a combination of metals consisting essentially of from 5 to 95 parts by weight gold and from 95 to 5 parts by weight total of at least one metal selected from the group consisting of ruthenium, rhodium, palladium, osmium, iridium, and platinum, wherein the combination of metals constitutes between about 0.1 to about 10% by weight of the catalyst and is prepared by the method of claim 2.

4. The catalyst of claim 3 wherein the catalyst contains less than 200 ppm phosphorus.

5. The catalyst of claim 4, wherein the catalyst contains less than 200 ppm sulfur.

6. The catalyst of claim 5 wherein the catalyst contains less than 100 ppm potassium, less than 100 ppm sodium, and less than 100 ppm iron.

7. The catalyst of claim 3 wherein the catalyst contains less than 100 ppm potassium, less than 100 ppm sodium, and less than 100 ppm iron.

8. The catalyst of claim 3 wherein the combination of metals consists essentially of gold and palladium.

9. The catalyst of claim 3 wherein the catalyst is a carbon-supported alloy catalyst in which the alloy consists essentially of from 50 to 70 weight percent gold and from 50 to 30 weight percent palladium.

* * * * *